United States Patent

Krämer et al.

[11] 4,359,470
[45] Nov. 16, 1982

[54] ACYLATED TRIAZOLYL-γ-FLUOROPINACOLYL DERIVATIVES AND THEIR USE AS FUNGICIDES

[75] Inventors: Wolfgang Krämer, Wuppertal; Karl Büchel, Burscheid; Jörg Stetter, Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 187,866

[22] Filed: Sep. 17, 1980

[30] Foreign Application Priority Data

Sep. 24, 1979 [DE] Fed. Rep. of Germany ....... 2938534

[51] Int. Cl.³ ................. A01N 43/64; C07D 249/08; C07F 1/08; C07F 3/06
[52] U.S. Cl. ................................. 424/269; 424/245; 548/101; 548/262; 260/456 R; 568/308; 568/419
[58] Field of Search .................. 548/101, 269, 341; 424/245, 269, 273 R

[56] References Cited

U.S. PATENT DOCUMENTS 4,254,132  3/1981  Kramer et al. .................. 424/269

FOREIGN PATENT DOCUMENTS 2811919  9/1979  Fed. Rep. of Germany ...... 424/269

Primary Examiner—Alton D. Rollins
Attorney, Agent, or Firm—Sprung, Horn, Kramer & Woods

[57] ABSTRACT

Fungicidally active acylated triazolyl-γ-fluoropinacolyl derivatives of the formula

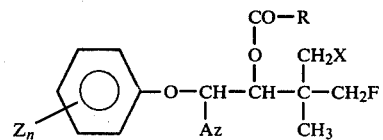

in which
Az represents 1,2,4-triazol-1-yl or 1,2,4-triazol-4-yl,
R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenoalkylamino, alkoxycarbonylamino or alkoxyalkylamino,
X represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro, each Z being selected independently, and
n represents 0 or an interger from 1 to 5, or a physiologically acceptable acid addition salt or metal salt complex thereof.

11 Claims, No Drawings

ACYLATED TRIAZOLYL-γ-FLUOROPINACOLYL DERIVATIVES AND THEIR USE AS FUNGICIDES

The present invention relates to certain new acylated triazolyl-γ-fluoropinacolyl derivatives, to a process for their preparation and to their use as fungicides.

It has already been disclosed that acylated 1-triazolyl-2-hydroxy-butane derivatives, such as, in particular, 2-acyloxy-3,3-dimethyl-1-phenoxy-1-(1,2,4-triazol-1-yl)-butanes which are substituted in the phenyl part, have good fungicidal properties (see DE-OS (German Published Specification) No. 2,600,799 [Le A 16 838]). However, their action is not always completely satisfactory, especially when small amounts and low concentrations are applied.

The present invention now provides, as new compounds, the acylated triazolyl-γ-fluoropinacolyl derivatives of the general formula

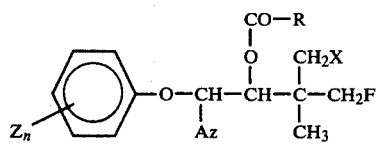
(I)

in which
Az represents 1,2,4-triazol-1-yl or 1,2,4-triazol-4-yl,
R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenoalkylamino, alkoxycarbonylamino or alkoxyalkylamino,
X represents hydrogen or fluorine,
Z represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro, each Z being selected independently, and
n represents 0 or an integer from 1 to 5, and physiologically acceptable acid addition salts and metal salt complexes thereof.

The compounds of the formula (I) have two asymmetric carbon atoms; they can thus exist in the erythro-form and in the threo-form. In both cases, they exist predominantly as racemates.

The invention also provides a process for the preparation of an acylated triazolyl-γ-fluoropinacolyl derivative of the formula (I), in which a 1-triazolyl-2-hydroxybutane derivative of the general formula

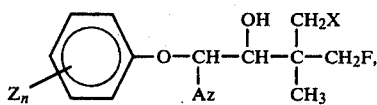
(II)

in which
Az, X, Z and n have the meanings indicated above,
(a) is reacted with an acid halide of the general formula Hal—CO—R (III), in which R has the meaning indicated above and
Hal represents halogen, especially chlorine or bromine, if appropriate in the presence of a solvent and if appropriate in the presence of an acid-binding agent, or (b) is reacted with an acid anhydride of the general formula

R—CO—O—CO—R (IV), in which
R has the meaning indicated above, in the presence of a solvent and if appropriate in the presence of a catalyst, or (c) is reacted with a ketene of the general formula

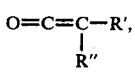
(V)

in which
R' and R'' are identical or different and each represent hydrogen, alkyl, alkoxy, halogen, halogenoalkyl, alkenyl or optionally substituted phenyl, in the presence of a solvent and if appropriate in the presence of a catalyst, or (d) is reacted with an isocyanate of the general formula

O=C=N—R''' (VI), in which
R''' represents alkyl, halogenoalkyl, alkoxycarbonyl, alkoxyalkyl or optionally substituted phenyl, in the presence of a solvent and if appropriate in the presence of a catalyst.

The acylated triazolyl-γ-fluoropinacolyl derivatives of the formula (I) which are obtainable according to the invention can furthermore be converted into salts by reaction with acids, and the corresponding metal salt complexes can be obtained by reaction with metal salts.

The acylated triazolyl-γ-fluoropinacolyl derivatives of the formula (I) have powerful fungicidal properties. Surprisingly, the compounds according to the invention exhibit a considerably more powerful action than the acylated triazolyl-2-hydroxy-butane derivatives which are known from the state of the art and are closely related compounds chemically and from the point of view of their action. The substances according to the invention thus represent an enrichment of the art.

The formula (I) provides a general definition of the acylated triazolyl-γ-fluoropinacolyl derivatives according to the invention. Preferably, in this formula, R represents straight-chain or branched alkyl with 1 to 8 (especially 1 to 6) carbon atoms, straight-chain or branched alkenyl or alkynyl with in either case 2 to 4 carbon atoms, halogenoalkyl with 1 to 2 carbon atoms and 1 to 5 halogen atoms (especially fluorine or chlorine), alkoxy with 1 to 4 carbon atoms, alkoxyalkyl with 1 to 4 carbon atoms in each alkyl part, cycloalkyl with 5 to 7 carbon atoms (especially cyclohexyl), optionally substituted phenyl or phenylalkyl or phenoxyalkyl, either of which is optionally substituted in the phenyl part and has up to 2 carbon atoms in the alkyl part, the preferred substituents on the phenyl part in the last three cases being selected from halogen, cyano, nitro and alkyl or alkoxy with in either case 1 to 2 carbon atoms, or R represents alkylamino with 1 to 12 carbon atoms, dialkylamino with 1 to 4 (especially 1 or 2) carbon atoms in each alkyl part, halogenoalkylamino with up to 4 carbon atoms and up to 5 identical or different halogen atoms (especially fluorine or chlorine atoms), or alkoxycarbonylamino with 1 to 4 carbon atoms in the alkyl part, alkoxyalkylamino with 1 to 4 carbon atoms in each alkyl part or optionally monosubstituted or polysubstituted phenylamino, the preferred substituents being selected from halogen, nitro, cyano, straight-chain or branched alkyl with 1 to 4 carbon atoms, alkoxy and alkylthio with in either case 1 to 2 carbon atoms, halogenoalkyl with up to 2 carbon atoms and up to 5 identical or different halogen atoms (for example fluorine and chlorine atoms) and alkoxycarbonylalkenyl with 1 to 4 carbon atoms in the alkyl part and 2 to 4 carbon atoms in the alkenyl part, X represents hydrogen or fluorine, Z represents halogen, cyano, nitro, straight-chain or branched alkyl with up to 4 carbon atoms, cycloalkyl with 5 to 7 carbon atoms (especially cyclohexyl), halogenoalkyl with up to 2 carbon atoms and up to 5 halogen atoms (especially fluorine or chlorine atoms), alkoxycarbonyl with a total of up to 5 carbon atoms, alkoxy or alkylthio with in either case up to 2 carbon atoms, or optionally substituted phenyl or phenoxy, in either case the preferred substituents being selected from halogen, amino, cyano, nitro and alkyl with 1 to 2 carbon atoms, or Z represents optionally substituted phenylalkyl with 1 or 2 carbon atoms in the alkyl part, the preferred substituent in the alkyl part being alkylcarbonyloxy with a total of up to 3 carbon atoms, and the preferred substituents in the phenyl part being selected from halogen, nitro and cyano, and n represents O or an integer from 1 to 3.

Az preferably represents 1,2,4-triazol-1-yl or 1,2,4-triazol-4-yl.

Very particularly preferred compounds of the formula (I) are those in which R represents methyl, ethyl, isobutyl, chloromethyl, dichloromethyl, chloroethyl, chloropropyl, methacrylyl, cyclohexyl, optionally monosubstituted or polysubstituted phenyl, benzyl or phenoxymethyl with chlorine, bromine, methyl or methoxy as substituents, and furthermore methoxy, ethoxy, isopropoxy, butoxy or isobutoxy, methyl- or ethylamino, dimethylamino, phenylamino, chlorophenylamino, chloroethylamino, methoxycarbonylamino, ethoxycarbonylamino or methoxymethylamino; X represents hydrogen or fluorine; Z represents chlorine, bromine, methyl, ethyl, cyclohexyl, methoxy, methylthio, trifluoromethyl, methoxycarbonyl, cyano, nitro or phenyl, benzyl or phenoxy which is optionally substituted by chlorine; and n represents 0, 1 or 2.

The following compounds of the general formula (I) may be mentioned specifically, in addition to those mentioned later in the preparative examples and in Table 3 (Az represents either 1,2,4-triazol-1-yl or 1,2,4-triazol-4-yl):

TABLE 1

$$Z_n\text{—}\underset{}{\bigcirc}\text{—O—CH(Az)—CH(O—CO—R)—C(CH}_3\text{)(CH}_2\text{X)—CH}_2\text{F} \quad (I)$$

| R | X | $Z_n$ |
|---|---|---|
| —CHCl$_2$ | H | 4-Cl |
| —CH$_2$Cl | H | 4-Cl |

TABLE 1-continued $$Z_n\text{—}\underset{}{\bigcirc}\text{—O—CH(Az)—CH(O—CO—R)—C(CH}_3\text{)(CH}_2\text{X)—CH}_2\text{F} \quad (I)$$

| R | X | $Z_n$ |
|---|---|---|
| —CH$_3$ | H | 4-phenyl |
| —NH—C$_6$H$_5$ | H | 4-phenyl |
| —NH—C$_6$H$_4$—Cl | H | 4-phenyl |
| —NHCH$_3$ | H | 4-phenyl |
| —NHCH$_3$ | H | 4-Cl; 2-CH$_3$ |
| —NHCH$_3$ | H | 2-Cl |
| —NHC$_2$H$_5$ | H | 4-phenyl |
| —C$_4$H$_9$—i | H | 4-Br |
| —CH$_3$ | H | 2,4-Cl$_2$ |
| —C$_2$H$_5$ | H | 2,4-Cl$_2$ |
| —CH$_3$ | H | 4-OCH$_3$ |
| —CH$_2$Cl | H | 3-CF$_3$ |
| —CHCl$_2$ | H | 4-CO—OCH$_3$ |
| —NHCH$_2$OCH$_3$ | H | 4-phenyl |
| —NHCH$_2$OC$_2$H$_5$ | H | 4-phenyl |
| —NH—COOCH$_3$ | H | 4-phenyl |
| —NH—COOC$_2$H$_5$ | H | 4-phenyl |
| —N(CH$_3$)$_2$ | H | 4-phenyl |
| —OCH$_3$ | H | 4-phenyl |
| —CH$_3$ | H | 4-phenyl-Cl |
| —CH$_3$ | H | 4-O-phenyl |
| —CH$_3$ | H | 4-O-phenyl-Cl |
| —CH$_3$ | H | 4-CN |
| —CH$_3$ | H | 4-NO$_2$ |
| —CH$_2$OC$_2$H$_5$ | H | 2,4-Cl$_2$ |
| —NHCH(CH$_3$)$_2$ | H | 2,4-Cl$_2$ |
| —NH—CH$_2$OCH$_3$ | H | 2,4-Cl$_2$ |
| —OC$_2$H$_5$ | H | 2,4-Cl$_2$ |
| —C(CH$_3$)=CH$_2$ | H | 2,4-Cl$_2$ |
| —CH$_2$—CH(CH$_3$)$_2$ | H | 2,4-Cl$_2$ |

TABLE 1-continued $$\text{(I)}\quad Z_n\text{—}\underset{}{\bigcirc}\text{—O—CH}(\text{Az})\text{—}\underset{\text{CH}_3}{\overset{\text{CO—R / CH}_2X}{\text{C}}}\text{—CH}_2F$$

| R | X | $Z_n$ |
|---|---|---|
| —CH$_2$—C$_6$H$_5$ | H | 2,4-Cl$_2$ |
| —CH$_2$—CH$_2$Cl | H | 2,4-Cl$_2$ |
| —CH$_2$—CH$_2$—CH$_2$Cl | H | 2,4-Cl$_2$ |
| —NH—C$_6$H$_4$—Cl | H | 2,4-Cl$_2$ |
| —CHCl$_2$ | H | 2,4-Cl$_2$ |
| —CH$_2$Cl | H | 2,4-Cl$_2$ |
| —C$_6$H$_4$—OCH$_3$ | H | 2,4-Cl$_2$ |
| —CH$_2$—O—C$_6$H$_3$Cl$_2$ | H | 2,4-Cl$_2$ |
| —C$_6$H$_{11}$ (cyclohexyl) | H | 2,4-Cl$_2$ |
| —C$_6$H$_5$ | H | 2,4-Cl$_2$ |
| —C$_6$H$_4$—Cl | H | 2,4-Cl$_2$ |
| —CH$_2$OC$_2$H$_5$ | H | 4-Cl |
| —NH—CH(CH$_3$)$_2$ | H | 4-Cl |
| —NH—CH$_2$OCH$_3$ | H | 4-Cl |
| —OC$_2$H$_5$ | H | 4-Cl |
| —C(CH$_3$)=CH$_2$ | H | 4-Cl |
| —CH$_2$—CH(CH$_3$)$_2$ | H | 4-Cl |
| —CH$_2$—C$_6$H$_5$ | H | 4-Cl |
| —CH$_2$—CH$_2$Cl | H | 4-Cl |
| —CH$_2$—CH$_2$—CH$_2$Cl | H | 4-Cl |
| —NH—C$_6$H$_4$—Cl | H | 4-Cl |
| —C$_6$H$_4$—OCH$_3$ | H | 4-Cl |
| —CH$_2$—O—C$_6$H$_3$Cl$_2$ | H | 4-Cl |
| —C$_6$H$_{11}$ (cyclohexyl) | H | 4-Cl |
| —C$_6$H$_5$ | H | 4-Cl |
| —C$_6$H$_4$—Cl | H | 4-Cl |
| —NHCH$_3$ | F | 2,4-Cl$_2$ |
| —NHCH$_3$ | F | 4-Cl |
| —CH$_3$ | F | 4-Cl |
| —NHCH$_3$ | F | C$_6$H$_5$ |
| —NHC$_2$H$_5$ | F | C$_6$H$_5$ |
| —NHCH$_2$OCH$_3$ | F | C$_6$H$_5$ |
| —NH—CH(CH$_3$)$_2$ | F | C$_6$H$_5$ |
| —CH$_2$OC$_2$H$_5$ | F | 4-Cl |
| —NH—CH(CH$_3$)$_2$ | F | 4-Cl |
| —NHCH$_2$OCH$_3$ | F | 4-Cl |
| —OC$_2$H$_5$ | F | 4-Cl |
| —C(CH$_3$)=CH$_2$ | F | 4-Cl |
| —CH$_2$—CH(CH$_3$)$_2$ | F | 4-Cl |
| —CH$_2$—C$_6$H$_5$ | F | 4-Cl |
| —CH$_2$—CH$_2$Cl | F | 4-Cl |
| —CH$_2$—CH$_2$—CH$_2$Cl | F | 4-Cl |
| —NH—C$_6$H$_4$—Cl | F | 4-Cl |
| —CHCl$_2$ | F | 4-Cl |
| —CH$_2$Cl | F | 4-Cl |
| —C$_6$H$_4$—OCH$_3$ | F | 4-Cl |
| —CH$_2$—O—C$_6$H$_3$Cl$_2$ | F | 4-Cl |
| —C$_6$H$_{11}$ (cyclohexyl) | F | 4-Cl |
| —C$_6$H$_5$ | F | 4-Cl |
| —C$_6$H$_4$—Cl | F | 4-Cl |
| —CH$_2$OC$_2$H$_5$ | F | 2,4-Cl$_2$ |
| —NH—CH(CH$_3$)$_2$ | F | 2,4-Cl$_2$ |
| —NH—CH$_2$OCH$_3$ | F | 2,4-Cl$_2$ |
| —OC$_2$H$_5$ | F | 2,4-Cl$_2$ |
| —C(CH$_3$)=CH$_2$ | F | 2,4-Cl$_2$ |
| —CH$_2$—CH(CH$_3$)$_2$ | F | 2,4-Cl$_2$ |
| —CH$_2$—C$_6$H$_5$ | F | 2,4-Cl$_2$ |
| —CH$_2$—CH$_2$Cl | F | 2,4-Cl$_2$ |
| —CH$_2$—CH$_2$—CH$_2$Cl | F | 2,4-Cl$_2$ |

TABLE 1-continued

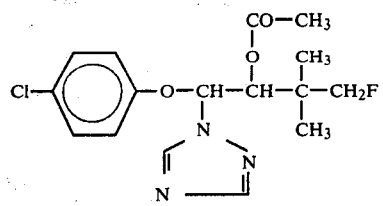

| R | X | $Z_n$ |
|---|---|---|
| —NH—⟨◯⟩—Cl | F | 2,4-Cl$_2$ |
| —CHCl$_2$ | F | 2,4-Cl$_2$ |
| —CH$_2$Cl | F | 2,4-Cl$_2$ |
| —⟨◯⟩—OCH$_3$ | F | 2,4-Cl$_2$ |
| —CH$_2$—O—⟨◯⟩(Cl)(Cl) | F | 2,4-Cl$_2$ |
| ⟨H⟩— | F | 2,4-Cl$_2$ |
| ⟨◯⟩— | F | 2,4-Cl$_2$ |
| —⟨◯⟩—Cl | F | 2,4-Cl$_2$ |

If, for example, 1-(4-chlorophenoxy)-1-(1,2,4-triazol-1-yl)-3,3-dimethyl-4-fluoro-butan-2-ol and dichloroacetyl chloride are used as starting substances in process variant (a), the course of the reaction can be represented by the following equation:

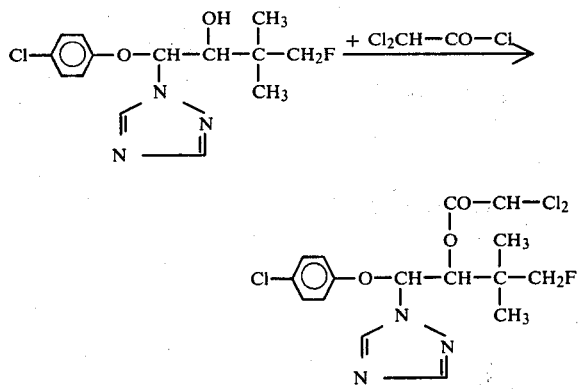

If, for example, 1-(4-chlorophenoxy)-1-(1,2,4-triazol-1-yl)-3,3-dimethyl-4-fluoro-butan-2-ol and acetic anhydride are used as starting substances in process variant (b), the course of the reaction can be represented by the following equation:

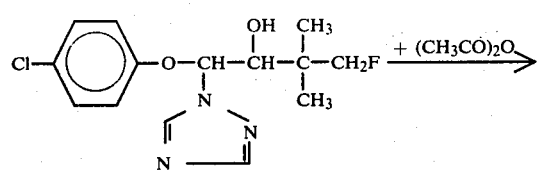

If, for example, 1-(2,4-dichlorophenoxy)-1-(1,2,4-triazol-1-yl)-3,3-dimethyl-4-fluoro-butan-2-ol and 4-chlorophenyl isocyanate are used as starting substances in process variant (d), the course of the reaction can be represented by the following equation:

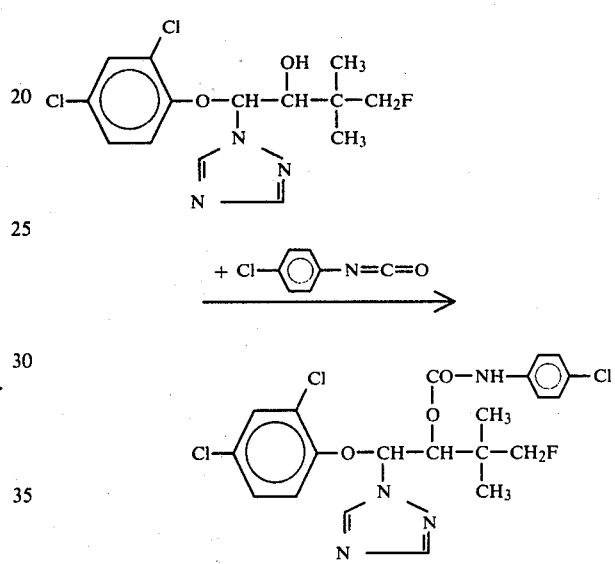

Reactions of 1-triazolyl-2-hydroxy-butane derivatives of the formula (II) with a ketene of the formula (V) in process variant (e) can be formulated in a corresponding manner.

The formula (II) provides a general definition of the 1-triazolyl-2-hydroxy-butane derivatives to be used as starting substances for all process variants. In this formula, Az, X, Z and the index n preferably have those meanings which have already been mentioned as preferred in connection with the description of the compounds of the formula (I).

The 1-triazolyl-2-hydroxy-butane derivatives of the formula (II) have not hitherto been disclosed in the literature; however, they are the subject of German Patent Application P 29 18 894.1 [Le A 19 618] of 10.5.1979, and they can be prepared by reacting halogenoether ketones of the general formula

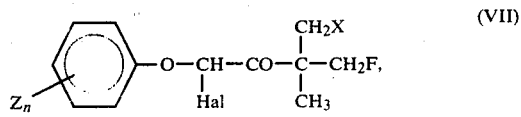

(VII)

in which

X, Z and n have the meanings indicated above and

Hal represents halogen, preferably chlorine or bromine, with 1,2,4-triazole in the presence of an acid-binding agent, for example sodium carbonate or an excess of triazole, and if appropriate in the presence of an inert organic solvent, for example acetone or acetonitrile, at temperatures between 60° and 120° C., and reducing the resulting keto derivatives by known methods, for example by reaction with complex hydrides, especially sodium borohydride, if appropriate in the presence of a polar organic solvent, for example an alcohol, at temperatures between 0° and 30° C., or by reaction with aluminum isopropylate in the presence of an inert organic solvent, for example isopropanol, at temperatures between 20° and 120° C. Working up is carried out in the customary manner.

The halogenoether ketones of the formula (VII) have not hitherto been disclosed in the literature. However, they are also the subject of the above-mentioned earlier application and can be obtained by a process (see, for example, DE-OS (German Published Specification) 2,632,603 [Le A 17 273]), for example by reacting known phenols of the general formula $$Z_n \text{—} \underset{}{\text{C}_6\text{H}_4} \text{—OH,} \quad (VIII)$$

in which
Z and n have the meanings indicated above, with a halogenoketone of the general formula $$\text{Hal}'\text{—CH}_2\text{—CO—}\underset{\underset{\text{CH}_2\text{X}}{|}}{\overset{\overset{\text{CH}_2\text{F}}{|}}{\text{C}}}\text{—CH}_3, \quad (IX)$$

in which
X has the meaning indicated above and
Hal′ represents chlorine or bromine. The active hydrogen atom which still remains is then replaced by halogen in the customary manner (see also the preparative examples).

The halogenoketones of the formula (IX) also have not hitherto been disclosed in the literature and are also the subject of the above-mentioned earlier application. However, they can be obtained in a generally customary and known manner by adding chlorine or bromine to fluorine derivatives of 3,3-dimethyl-butan-2-one, of the general formula $$\text{CH}_3\text{—CO—}\underset{\underset{\text{CH}_2\text{X}}{|}}{\overset{\overset{\text{CH}_2\text{F}}{|}}{\text{C}}}\text{—CH}_3, \quad (X)$$

in which
X has the meaning indicated above, at room temperature in the presence of an inert organic solvent, for example ether or a chlorinated hydrocarbon (see also the preparative examples), or by reacting the fluorine derivatives with customary chlorinating agents, for example sulphuryl chloride, at 20° to 60° C.

The fluorine derivatives of 3,3-dimethyl-butan-2-one, of the formula (X), also have not hitherto been disclosed in the literature. However, they are the subject of German Patent Application P 28 43 767 [Le A 18 985] of 6.10.1978. The fluorine derivatives of 3,3-dimethyl-butan-2-one, of the formula (X), are obtained when sulphonic acid esters of the general formula $$\text{CH}_3\text{—CO—}\underset{\underset{\text{CH}_2\text{Y}}{|}}{\overset{\overset{\text{CH}_2\text{—O—SO}_2\text{—R}^1}{|}}{\text{C}}}\text{—CH}_3, \quad (XI)$$

in which
$R^1$ represents alkyl with 1 to 4 carbon atoms, especially methyl, or aryl with 6 to 12 carbon atoms, especially phenyl or tolyl, and
Y represents hydrogen or the group —O—SO$_2$—R$^1$, are reacted with metal fluorides, for example sodium fluoride and potassium fluoride, in the presence of a polar organic solvent, for example di-, tri- or tetraethylene glycol, at temperatures between 80° and 250° C. (see also the preparative examples).

Sulphonic acid esters of the formula (XI) are known (J. Org. Chem. 35, 2391 (1970)) and can be prepared from the corresponding hydroxybutanones and sulphochlorides in the presence of bases, by processes which are known from the literature (see, for example, Houben-Weyl, Methoden der Org. Chemie (Methods of Organic Chemistry), Volume IX, pages 388 and 663, and the statements in the preparative examples).

Specific examples of the starting substances of the formula (II) which may be mentioned are (Az represents either 1,2,4-triazol 1-yl or 1,2,4-triazol-4-yl):

TABLE 2

$$Z_n\text{—}\underset{}{\text{C}_6\text{H}_4}\text{—O—CH—}\underset{\underset{\text{Az}}{|}}{\overset{\overset{\text{OH}}{|}}{\text{CH}}}\text{—}\underset{\underset{\text{CH}_3}{|}}{\overset{\overset{\text{CH}_2\text{X}}{|}}{\text{C}}}\text{—CH}_2\text{F} \quad (II)$$

| $Z_n$ | X | $Z_n$ | X |
|---|---|---|---|
| — | H | — | F |
| 2-Cl | H | 2-Cl | F |
| 3-Cl | H | 3-Cl | F |
| 4-Cl | H | 4-Cl | F |
| 2-F | H | 2-F | F |
| 3-F | H | 3-F | F |
| 4-F | H | 4-F | F |
| 2-Br | H | 2-Br | F |
| 3-Br | H | 3-Br | F |
| 4-Br | H | 4-Br | F |
| 2,4-Cl$_2$ | H | 2,4-Cl$_2$ | F |
| 2-CH$_3$ | H | 2-CH$_3$ | F |
| 4-CH$_3$ | H | 4-CH$_3$ | F |
| 2-Cl,4-CH$_3$ | H | 2-Cl,4-CH$_3$ | F |
| 4-Cl,2-CH$_3$ | H | 4-Cl,2-CH$_3$ | F |
| 4-I | H | 4-I | F |
| 4-CN | H | 4-CN | F |
| 2-NO$_2$ | H | 2-NO$_2$ | F |
| 4-COOCH$_3$ | H | 4-COOCH$_3$ | F |
| 4-COOC$_2$H$_5$ | H | 4-COOC$_2$H$_5$ | F |
| 4-C$_6$H$_5$ | H | 4-C$_6$H$_5$ | F |
| 2-C$_6$H$_5$ | H | 2-C$_6$H$_5$ | F |
| 4-C$_6$H$_4$-Cl | H | 4-C$_6$H$_4$-Cl | F |

The formula (III) provides a general definition of the acid halides also to be used as starting substances for process variant (a). In this formula, R preferably represents those radicals which have already been mentioned as preferred in connection with the description of the compounds of the formula (I).

Acid halides of the formula (III) are known and can be prepared by customary processes, for example by reacting carboxylic acids or alkali metal salts thereof with acid halides of phosphorus or sulphur. These methods are known from the general textbooks of organic chemistry.

The formula (IV) provides a general definition of the acid anhydrides also to be used as starting substances for process variant (b). In this formula, R preferably represents those radicals which have already been mentioned as preferred in connection with the description of the compounds of the formula (I).

The acid anhydrides of the formula (IV) are known, or they can be prepared by known processes, for example by the action of acid chlorides on the alkali metal salts of carboxylic acids. These processes are generally known.

The formula (V) provides a general definition of the ketenes also to be used as starting substances for process variant (c). In this formula, R' and R" are identical or different and preferably represent hydrogen, alkyl with 1 to 7, especially 1 to 5, carbon atoms, alkenyl with up to 3 carbon atoms or halogenomethyl with 1 to 3 halogen atoms, especially fluorine and chlorine. R' and R" also preferably represent halogen, especially chlorine or bromine, alkoxy with 1 to 3 carbon atoms or optionally monosubstituted or polysubstituted phenyl, preferred substituents being halogen, cyano, nitro and alkyl with 1 to 2 carbon atoms.

Ketenes of the formula (V) are known and be prepared by known processes, for example by thermolysis of ketones or by dehydration of carboxylic acids (see Houben-Weyl, "Methoden der organischen Chemie" ("Methods of Organic Chemistry"), Volume 7/4, Georg Thieme Verlag).

The formula (VI) provides a general definition of the isocyanates also to be used as starting substances for process variant (d). In this formula, R''' preferably represents straight-chain or branched alkyl with 1 to 12 carbon atoms, halogenoalkyl with up to 4 carbon atoms and up to 5 identical or different halogen atoms, especially fluorine and chlorine atoms, or alkoxycarbonyl or alkoxyalkyl with in either case 1 to 4 carbon atoms in each alkyl part. R''' also preferably represents optionally monosubstituted or polysubstituted phenyl, preferred substituents being halogen, nitro, cyano, straight-chain or branched alkyl with 1 to 4 carbon atoms, alkoxy and alkylthio with in each case 1 or 2 carbon atoms, halogenoalkyl with up to 2 carbon atoms and up to 5 identical or different halogen atoms, especially fluorine and chlorine atoms, and alkoxycarbonylalkenyl with 1 to 4 carbon atoms in the alkyl part and 2 to 4 carbon atoms in the alkenyl part.

Isocyanates of the formula (VI) are known and can be prepared by generally customary and known processes, for example by reacting amines with phosgene and then heating the product.

Preferred solvents for the reaction according to process variant (a) are any of the inert organic solvents. These include, as preferences, nitriles, such as propionitrile, and in particular acetonitrile; ethers, such as tetrahydrofuran or dioxane; esters, such as ethyl acetate; aromatic hydrocarbons, such as benzene or toluene; and halogenated hydrocarbons, such as methylene chloride, carbon tetrachloride or chloroform. For simplicity, the acid chloride employed can also be used as the solvent, in which case an appropriate excess becomes necessary.

The reaction temperatures can be varied within a substantial range in carrying out process variant (a). In general, the reaction is carried out between 0° and 100° C., preferably between 20° and 85° C. If a solvent is present, the reaction is optionally carried out at the boiling point of the particular solvent.

If appropriate, process variant (a) can be carried out in the presence of an acid-binding agent (hydrogen halide acceptor); any of the customary acid-binding agents can be used here. These include organic bases, preferably tertiary amines, for example triethylamine; and furthermore inorganic bases, for example alkali metal hydroxides and alkali metal carbonates.

Equimolar amounts of the reactants are preferably used in carrying out process variant (a). The resultant compound of the formula (I) is obtained in the form of its hydrohalide and can be isolated as such by precipitating it by adding an organic solvent, for example hexane, filtering it off and, if appropriate, purifying it by recrystallization. The resultant compound of the formula (I) can also be isolated in the form of its free base, by adding aqueous sodium bicarbonate solution to the reaction mixture and isolating the base by customary methods.

Preferred diluents for the reaction according to process variant (b) are any of the inert organic solvents. These include, as preferences, the solvents listed for process variant (a) and the acid anhydrides of the formula (IV) used in each case.

Preferred catalysts which can be used in process variant (b) are any of the customary acid and basic catalysts, for example sulphuric acid, hydrogen chloride, hydrogen bromide, boron trifluoride, zinc chloride, sodium acetate, sodium benzoate, sodium carbonate, calcium oxide and magnesium oxide.

The reaction temperatures can be varied within a substantial range in carrying out process variant (b). In general, the reaction is carried out between 0° and 150° C., preferably between 80° and 120° C.

Equimolar amounts of the reactants are preferably used in carrying out process variant (b). For simplicity, the acid anhydride of the formula (IV) employed can also be used as the solvent, in which case an appropriate excess becomes necessary. The compounds of the formula (I) are isolated in the customary manner.

Preferred diluents for the reaction according to process variant (c) are any of the inert organic solvents. These include, as preferences, the solvents listed for process variant (a).

Preferred catalysts which can be used in process variant (c) are any of the customary acid and basic catalysts. These include, as preferences, the substances listed for process variant (b).

The reaction temperatures can be varied within a certain range in carrying out process variant (c). In general, the reaction is carried out between −10° and 70° C., preferably between 0° and 40° C.

Equimolar amounts of the reactants are preferably used in carrying out process variant (c). The compounds of the formula (I) are isolated by customary methods.

Preferred diluents for the reaction according to process variant (d) are any of the inert organic solvents. These include, as preferences, the solvents listed for process variant (a).

Preferred catalysts which can be used in process variant (d) are: tertiary bases, such as triethylamine and pyridine, or organo-tin compounds, such as dibutyl-tin dilaurate.

The reaction temperatures can be varied within a substantial range in carrying out process variant (d). In general, the reaction is carried out between 0° and 100° C., preferably between 20° and 40° C.

Equimolar amounts of the reactants are preferably used in carrying out process variant (d). To isolate the compounds of the formula (I), the solvent is distilled off and the residue is worked up by customary methods.

Any of the physiologically acceptable acids can be used for the preparation of acid addition salts of the compounds of the formula (I). These acids include, as preferences, hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid), and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of sub-groups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiologically acceptable acids. These include, as preferences, hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases and thus for combating Podosphaera species, for example the powdery mildew of apple causative organism (*Podosphaera leucotricha*), or Erysiphe species, for example the powdery mildew of cucumber causative organism (*Erysiphe cichoracearum*) or the powdery mildew of cereal causative organism (*Erysiphe graminis*); the compounds can also be used for combating other cereal diseases, such as cereal rust. It should be particularly emphasised that the active compounds according to the invention not only display a protective action but in some cases are also systemic. Thus, it is possible to protect plants against fungal attack if the active compound is fed to the above-ground parts of the plant via the soil and the root or the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations. It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

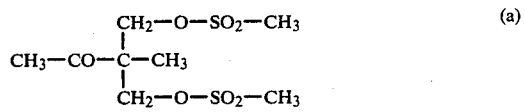
(a)

66 g (0.5 mol) of 3-oxo-2,2-bis-(hydroxymethyl)-butane (for the preparation, see Beilstein H 1, E III 3306, IV 4132 and J.Chem.Soc., London, 1932, 2671) were dissolved in 300 ml of 1,2-dichloroethane, 114.5 g (1 mol) of methanesulphonic acid chloride were added dropwise, and 158 g (2 mol) of pyridine were added dropwise at 0° to 5° C. The mixture was subsequently stirred at room temperature for 15 hours and then poured onto 600 ml of ice-water and 100 ml of concentrated hydrochloric acid. A solid thereby precipitated and was filtered off. The aqueous phase was extracted with 1,000 ml of methylene chloride; the solid was dissolved in the methylene chloride phase, the organic phase was dried over sodium sulphate, the solvent was distilled off under a waterpump vacuum and the residue was suspended in 200 ml of ether. The residue was filtered off and washed with 100 ml of ether. 100 g (about 70% of theory) of 2-acetyl-2-methylpropane-1,3-diol bismethanesulphonate of melting point 105°–108° C. were obtained.

(b)

400 ml of tetraethylene glycol and 46.4 g (0.8 mol) of potassium fluoride were initially introduced into a three-necked flask with a stirrer, dropping funnel and Liebig condenser with a cooled receiver, and the mixture was heated to 170° C. A waterpump vacuum (pressure: about 20 to 30 mbars) was applied to the adapter of the Liebig condenser. 57.6 g (0.2 mol) of 2-acetyl-2-methyl-propane-1,3-diol bismethanesulphonate, dissolved in 100 ml of tetraethylene glycol, were then added dropwise in the course of 45 minutes. The 3,3-bis-fluoromethyl-butan-2-one formed was distilled into the cooled receiver during the reaction. After the dropwise addition, distillation was continued for a further 1 hour at 175° C.

The distillate collected was then redistilled. 14 g (about 51.5% of theory) of 3,3-bisfluoromethyl-butan-2-one of boiling point 43°–46° C./12 mm Hg were obtained.

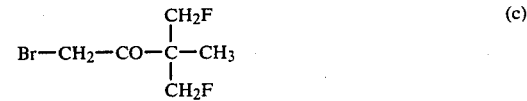
(c)

903 g of bromine were slowly added dropwise to a mixture of 757.0 g (5.58 mols) of 3,3-bisfluoromethyl-2-butanone and 4.5 liters of methylene chloride at 20° to 30° C., while cooling and stirring. The yellowish solution was subsequently stirred at 20° C. for a further 1 hour. After distilling off the solvent, the residue was distilled in vacuo. 1,030 g (86% of theory) of 3,3-bisfluoromethyl-1-bromo-butan-2-one of boiling point 49°–53° C./0.15 mm Hg were obtained.

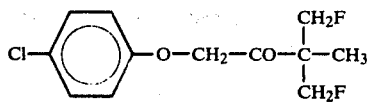

(d)

171.2 g (0.79 mol) of 3,3-bisfluoromethyl-1-bromo-butan-2-one were added dropwise to a stirred mixture of 102 g (0.79 mol) of p-chlorophenol and 110 g (0.79 mol) of powdered potassium carbonate in 500 ml of acetone at 20° to 30° C. The mixture was subsequently stirred at 40° C. for 4 hours, the inorganic salt was filtered off and the filtrate was concentrated. The residue was distilled under a high vacuum. 190.5 g (90% of theory) of 3,3-bisfluoromethyl-1-(4-chlorophenoxy)-butan-2-one of boiling point 113°–117° C./0.1 mm Hg were obtained.

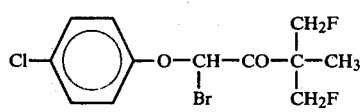

(e)

166 g (0.632 mol) of 3,3-bisfluoromethyl-1-(4-chlorophenoxy)-butan-2-one were dissolved in 500 ml of methylene chloride, and 100 g (0.625 mol) of bromine were added dropwise at 20° to 30° C., while stirring and cooling. The mixture was subsequently stirred at 20° C. for 2 hours. After distilling off the solvent in vacuo, the residue was crystallized from petroleum ether. 190 g (88% of theory) of 3,3-bisfluoromethyl-1-bromo-1-(4-chlorophenoxy)-butan-2-one of melting point 54°–57° C. were obtained.

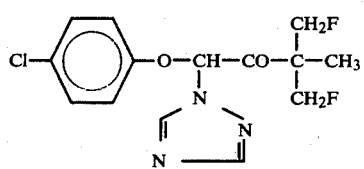

(f)

190 g (0.557 mol) of 3,3-bisfluoromethyl-1-bromo-1-(4-chlorophenoxy)-butan-2-one and 90 g (1.3 mols) of triazole were introduced into 800 ml of acetonitrile, the mixture was heated at 50° C. for 5 hours, the solvent was distilled off under a waterpump vacuum, the residue was taken up in one liter of methylene chloride and washed twice with 1,000 ml of water each time, the organic phase was dried over sodium sulphate and the solvent was distilled off. The residue was taken up in 500 ml of diisopropyl ether and the precipitate was filtered off. The mother liquor was distilled. 130.5 g (71% of theory) of 3,3-bisfluoromethyl-1-(4-chlorophenoxy)-1-(1,2,4-triazol-1-yl)-butan-2-one of boiling point 160°–66° C./0.2 mm Hg were obtained.

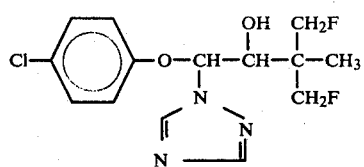

(g)

130.5 g (0.395 mol) of 3,3-bisfluoromethyl-1-(4-chlorophenoxy)-1-(1,2,4-triazol-1-yl)-2-butanone were dissolved in 800 ml of methanol, and 21 g (0.55 mol) of sodium borohydride were added in portions. The reaction solution was subsequently stirred for 15 hours and was then adjusted to a pH value of 3 with concentrated hydrochloric acid. The mixture was then stirred for 2 hours. After distilling off the solvent in vacuo, water/sodium bicarbonate were added to the residue and the mixture was extracted by shaking with 600 ml of methylene chloride. The combined organic phases were dried over sodium sulphate and concentrated in vacuo. The residue was crystallized with diisopropyl ether. 112 g (86% of theory) of 3,3-bisfluoromethyl-1-(4-chlorophenoxy)-1-(1,2,4-triazol-1-yl)-butan-2-ol of melting point 97°–102° C. were obtained.

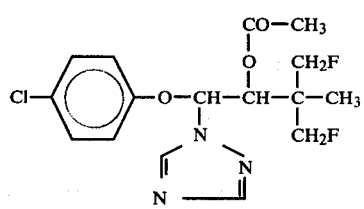

(h)

(1)

Process variant (b)

112 g (0.328 mol) of 3,3-bisfluoromethyl-1-(4-chlorophenoxy)-1-(1,2,4-triazol-1-yl)-butan-2-ol (as the diastereomeric mixture of the pure forms A and B) were dissolved in 500 ml of acetic anhydride. The solution was stirred at 100° C. for 16 hours, the excess acetic anhydride was distilled off in vacuo and the residue was taken up in 600 ml of methylene chloride. The organic phase was washed twice with 1.5 liters of water each time, dried over sodium sulphate and concentrated. The oily residue was subjected to fractional crystallization in diisopropyl ether. 48 g (38% of theory) of the A-form (Compound 1a) of 2-acetoxy-3,3-bisfluoromethyl-1-(4-chlorophenoxy)-1-(1,2,4-triazol-1-yl)-butane of melting point 130°–133° C. and 20.5 g (16% of theory) of the B-form (Compound 1b) of 2-acetoxy-3,3-bisfluoromethyl-1-(4-chlorophenoxy)-1-(1,2,4-triazol-1-yl)-butane of melting point 98° C. were obtained.

A-form and B-form in each case denote one of the two possible geometric isomers.

EXAMPLE 2

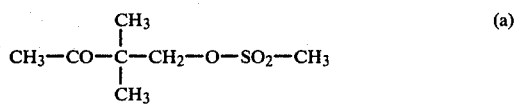

(a)

232 g (2 mols) of 3,3-dimethyl-4-hydroxy-2-butanone (for the preparation, see Beilstein H 1, E III, 3239, IV 4030 and Bull. Soc. Chim. France 1954, 2849) in 700 ml of absolute pyridine were reacted with 229 g (2 mols) of methanesulphonyl chloride at 0° to 5° C. After leaving the mixture to stand at 20° C. for 12 hours, it was diluted with methylene chloride and extracted by shaking with ice-water. The organic phase was dried and freed from the solvent in vacuo and the residue was fractionated over a column. 332 g (86% of theory) of 2,2-dimethyl-3-oxo-butyl methanesulphonate of boiling point 106°–120° C./0.12 mm Hg were obtained.

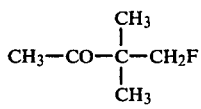 (b)

38.8 g (0.2 mol) of 2,2-dimethyl-2-oxobutyl methanesulphonate were added dropwise to a suspension, in a three-necked stirred flask with a descending condenser, of 23.2 g (0.4 mol) of dry potassium fluoride in 400 ml of distilled tetraethylene glycol at 160° C. and under 20 mbars in the course of 2 hours and the mixture was subsequently stirred for a further 2 hours. The reaction product which had been distilled out was condensed in a descending condenser and collected in a subsequent low temperature trap. 20.9 g (89% of theory) of 3,3-dimethyl-4-fluoro-2-butanone of boiling point 130°–134° C. were obtained.

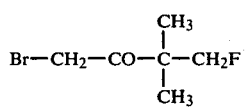 (c)

480 g of bromine were slowly added dropwise to a mixture of 354 g (3 mols) of 3,3-dimethyl-4-fluoro-2-butanone and 2,000 ml of ether at 20° to 30° C., while cooling and stirring. The yellowish solution was subsequently stirred at 20° C. for a further hour and 500 ml of water were then carefully added. The ether phase was separated off, washed several times with water and dried over sodium sulphate. After distilling off the solvent, the residue was distilled under a waterpump vacuum. 472 g (80% of theory) of 1-bromo-3,3-dimethyl-4-fluoro-2-butanone of boiling point 80°–90° C./11 mm Hg were obtained.

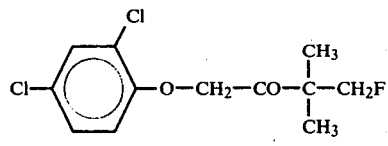 (d)

157 g (0.79 mol) of 1-bromo-3,3-dimethyl-4-fluoro-2-butanone were added dropwise to a stirred mixture of 129 g (0.79 mol) of 2,4-dichlorophenol and 110 g (0.79 mol) of powdered potassium carbonate in 500 ml of acetone at 20° to 30° C., while cooling. The mixture was subsequently stirred at 20° C. for 2 hours, the inorganic salt was filtered off and the filtrate was concentrated. 199.3 g (90% of theory) of 1-(2,4-dichlorophenoxy)-3,3-dimethyl-4-fluoro-2-butanone were obtained as an oil, which was further reacted directly.

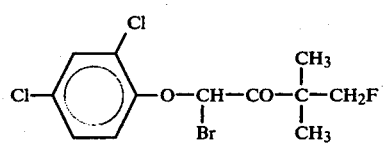 (e)

199.5 g (0.71 mol) of 1-(2,4-dichlorophenoxy)-3,3-dimethyl-4-fluoro-2-butanone were dissolved in 500 ml of chloroform, and 114 g (0.71 mol) of bromine were added dropwise at 20° C., while stirring and cooling. The mixture was subsequently stirred at 20° C. for 2 hours, 200 ml of water were carefully added and the chloroform phase was washed several times with ice-water and dried over sodium sulphate. After distilling off the solvent in vacuo, 205.2 g (78% of theory) of 1-bromo-1-(2,4-dichlorophenoxy)-3,3-dimethyl-4-fluoro-2-butanone was obtained as an oil, which was further reacted directly.

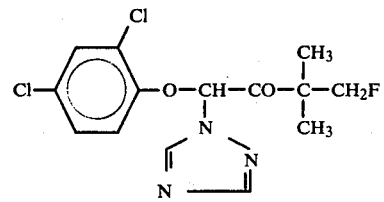 (f)

96.3 g (0.27 mol) of 1-bromo-1-(2,4-dichlorophenoxy)-3,3-dimethyl-4-fluoro-2-butanone were dissolved in 200 ml of acetonitrile and the solution was added dropwise to a boiling solution of 46 g (0.56 mol) of 1,2,4-triazole in 200 ml of acetonitrile. After heating the mixture under reflux for 20 hours, the solvent was removed in vacuo, the residue was taken up in methylene chloride, the methylene chloride mixture was washed several times with water and the organic phase was dried over sodium sulphate. After removing the solvent in vacuo, 83 g (89% of theory) of 1-(2,4-dichlorophenoxy)-3,3-dimethyl-4-fluoro-1-(1,2,4-triazol-1-yl)-2-butanone were obtained as an oil, which was further reacted directly.

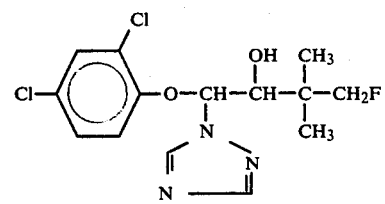 (g)

61.1 g (0.176 mol) of 1-(2,4-dichlorophenoxy)-3,3-dimethyl-4-fluoro-1-(1,2,4-triazol-1-yl)-2-butanone were dissolved in 250 ml of methanol, and 3 g (0.08 mol) of sodium borohydride were added in portions. The reaction solution was subsequently stirred for 1 hour and was then adjusted to a pH value of 3 with concentrated hydrochloric acid. After distilling off the solvent in vacuo, water was added to the residue and the mixture was extracted by shaking with methylene chloride. The combined organic phases were dried over sodium sulphate and concentrated in vacuo. The residue was crystallized with diethyl ether. 44.4 g (72% of theory) of 1-(2,4-dichlorophenyl)-3,3-dimethyl-4-fluoro-1-(1,2,4-triazol-1-yl)-2-butanol of melting point 98°–100° C. were obtained.

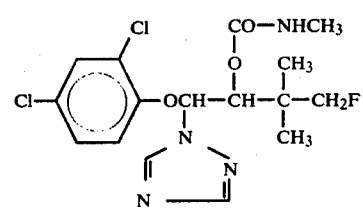 (h)

(2)

Process variant (d)

8.4 g (0.024 mol) of 1-(2,4-dichlorophenoxy)-3,3-dimethyl-4-fluoro-1-(1,2,4-triazol-1-yl)-butan-2-ol were dissolved in 100 ml of dioxane, and 2 ml of methyl isocyanate and 3.5 ml of triethylamine were added. The mixture was heated under reflux for 10 hours and concentrated by distilling off the solvent in vacuo. The residue was heated in 50 ml of ethyl acetate and the mixture was filtered. 8 g (86% of theory) of 1-(2,4-dichlorophenoxy)-3,3-dimethyl-4-fluoro-2-methylcarbamoyloxy-1-(1,2,4-triazol-1-yl)-butane were obtained in the form of colorless crystals of melting point 124°–27° C.

The following compounds of the general formula

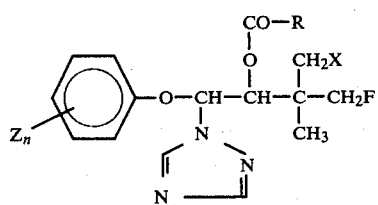

were obtained in a corresponding manner and according to process variants (a) to (d):

TABLE 3

| Compound No. | $Z_n$ | R | X | Melting point (°C.) |
|---|---|---|---|---|
| 3 | 4-Cl | —NHCH$_3$ | H | Oil |
| 4 | 4-Cl | —CH$_3$ | H | Oil |
| 5 | 4-Cl | —CH$_2$Cl | F | 123–25 (A-Form) |
| 6 | 4-Cl | —CHCl$_2$ | F | 214 (× ½ NDS) |
| 7 | 4-Cl | —NHCH$_3$ | F | 144–50 (A-Form) |
| 8 | 2,4-Cl$_2$ | —NHCH$_3$ | F | 131–34 (A-Form) |
| 9 | 4-F | —CH$_3$ | F | 136–38 (A-Form) |
| 10 | 2,4-Cl$_2$ | —CH$_3$ | F | 123–25 (A-Form) |
| 11 | 4-F | —CH$_2$Cl | F | 116–18 (A-Form) |
| 12 | 2,4-Cl$_2$ | —CH$_2$Cl | F | 89–91 (A-Form) |
| 13 | 4-F | —CHCl$_2$ | F | 63–66 (A-Form) |
| 14 | 2,4-Cl$_2$ | —CHCl$_2$ | F | 98 (A-Form) |
| 15 | 4-F | —NHCH$_3$ | F | 181–90 (A-Form) |
| 16 | 4-F | —NH—CH$_2$OCH$_3$ | F | 172 (A-Form) (× ½ NDS) |
| 17 | 4-Cl-C$_6$H$_4$- | —CH$_3$ | F | 83–87 |
| 18 | C$_6$H$_5$- | —NH—CH$_3$ | F | 131–33 |
| 19 | C$_6$H$_5$- | —NH—C$_2$H$_5$ | F | 112–14 |
| 20 | C$_6$H$_5$- | —NH—CH(CH$_3$)$_2$ | F | 116–18 |
| 21 | 4-Cl | —NH—CH(CH$_3$)$_2$ | F | 110 |
| 22 | 2,4-Cl$_2$ | —NH—CH(CH$_3$)$_2$ | F | 121–22 |
| 23 | 4-Cl | —NH—C$_6$H$_4$—Cl | F | 133 |
| 24 | 2,4-Cl$_2$ | —NH—C$_6$H$_4$—Cl | F | 157–58 |
| 25 | 4-Cl | —C$_6$H$_4$—Cl | F | 150 |
| 26 | 4-C$_6$H$_5$ | —NH—CH$_2$—O—CH$_3$ | F | 180 (× ½ NDS) |
| 27 | 4-Cl | —NH—CH$_2$—O—CH$_3$ | F | 180–83 (× ½ NDS) |
| 28 | 2,4-Cl$_2$ | —NH—CH$_2$—O—CH$_3$ | F | 210 (× ½ NDS) |
| 29 | 4-Cl | —CH$_2$—C$_6$H$_5$ | F | 184–94 (× ½ NDS) |
| 30 | 4-Cl | —CH$_2$—O—C$_2$H$_5$ | F | 181–88 (× ½ NDS) |
| 31 | 4-Cl | C$_6$H$_5$ | F | 48–50 |
| 32 | 4-Cl | —C$_6$H$_4$—OCH$_3$ | F | 187–89 (× ½ NDS) |
| 33 | 4-Cl | —CH$_2$—O—C$_6$H$_4$—Cl | F | 205–10 (× ½ NDS) |
| 34 | 2,4-Cl$_2$ | C$_6$H$_5$ | F | 95–98 |
| 35 | 2,4-Cl$_2$ | —C$_6$H$_4$—Cl | F | 212–18 (× ½ NDS) |
| 36 | 2,4-Cl$_2$ | —CH$_2$CH$_2$CH$_2$Cl | F | 212–18 (× ½ NDS) |
| 37 | 4-Cl | —CH$_2$CH$_2$CH$_2$Cl | F | 78–81 |
| 38 | 2,4-Cl$_2$ | —C$_6$H$_4$—OCH$_3$ | F | 185–90 (× ½ NDS) |
| 39 | 4-Cl | —C(CH$_3$)=CH$_2$ | F | 191–98 (× ½ NDS) |
| 40 | 2,4-Cl$_2$ | cyclohexyl | F | 91–94 (A-Form) |
| 41 | 4-Cl | cyclohexyl | F | 173 (A-Form) |
| 42 | 2,4-Cl$_2$ | CN$_2$—C$_6$H$_5$ | F | 199–203 (× ½ NDS) |
| 43 | 2,4-Cl$_2$ | CH$_3$ | H | 145–8 |
| 44 | 4-Cl | CH$_2$Cl | H | 104–120 |

TABLE 3-continued

| Compound No. | $Z_n$ | R | X | Melting point (°C.) |
|---|---|---|---|---|
| 45 | 4-Cl | CHCl$_2$ | H | crystalline mass |

NOTE:
NDS = 1,5-naphthalene disulphonate.

The fungicidal activity of the compounds of this invention is illustrated by the following biotest examples wherein the compounds according to the present invention are each identified by the number (given in brackets) from the preparative examples hereinabove:

The known comparison compounds are identified as follows:

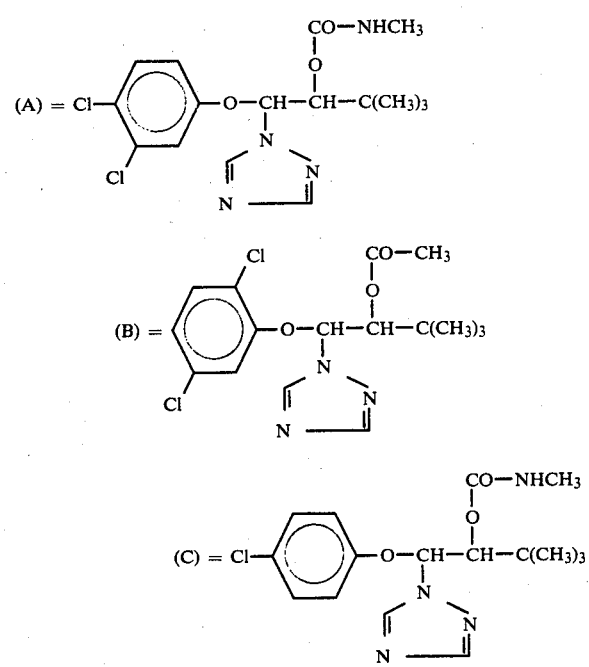

EXAMPLE 3

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew moist. After drying, the barley plants were dusted with spores of Erysiphe graminis var. hordei.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound the lower was the degree of mildew infection.

In this test, for example, the following compounds exhibited a very good action which was superior to that of the compound (A) known from the prior art: compounds (1a), (3), (4), (2) and (1b).

EXAMPLE 4

Powdery mildew of barley (Erysiphe graminis var. hordei) (fungal disease of cereal shoots)/systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of Erysiphe graminis var. hordei and grown on at 21-22 deg. C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, for example, the following compounds exhibited a very good action which was superior to that of the compound (B) known from the prior art: compounds (1a) and (4).

EXAMPLE 5

Shoot treatment test/cereal rust (leaf-destructive mycosis)/protective

To produce a suitable preparation of active compound, 0.25 part by weight of active compound was taken up in 25 parts by weight of dimethylformamide and 0.06 part by-weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of Puccinia recondita in 0.1% strength aqueous agar. After the spore suspension had dried on, the wheat plants were sprayed with the preparation of active compound until dew-moist and were placed, for incubation, in a greenhouse for 24 hours at about 20 deg. C. and 100% relative atmospheric humidity.

After 10 days' dwell time of the plants at a temperature of 20 deg. C. and 80-90% atmospheric humidity, the occurrence of rust pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of rust infection.

In this test, for example, the following compounds exhibited a very good action which was superior to that of the compound (B) known from the prior art: compounds (1a) and (4).

EXAMPLE 6

Erysiphe test (cucumber)/protective
Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23-24 degrees C. and at a relative atmospheric humidity of about 75%.

After 12 days, the infection of the cucumber plants was determined. The assessment data were converted to percent infection. 0% meant no infection; 100% meant that the plants were totally infected.

In this test, for example, the following compound exhibited a very good action which was superior to that of the compound (C) known from the prior art: compound (1a).

EXAMPLE 7

Podosphaera test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the static amount of emulsifier.

Young apple seedlings in the 4-6 leaf stage were sprayed with the spray liquid until dripping wet. The plants remained in a greenhouse for 24 hours at 20 deg. C. and at a relative atmospheric humidity of 70%. They were then inoculated by dusting the conidia of the apple powdery mildew causative organism (*Podosphaera leucotricha*) and placed in a greenhouse at a temperature of 21-23 deg. C. and at a relative atmospheric humidity of about 70%.

10 days after the inoculation, the infection of the seedlings was determined. The assessment data were converted to % infection. 0% meant no infection; 100% meant that the plants were completely infected.

In this test, for example, the following compounds exhibited a very good action which was significantly superior to that of the compound (C) known from the prior art: compounds (1a), (4) and (1b).

It will be appreciated that the instant specification and examples are set forth by way of illustration and not limitation, and that various modifications and changes may be made without departing from the spirit and scope of the present invention.

We claim:

1. An acylated triazolyl-γ-fluoropinacolyl derivative of the formula

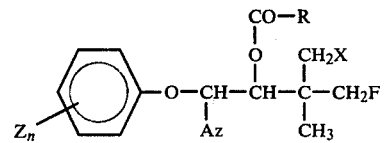

in which

Az represents 1,2,4-triazol-1-yl or 1,2,4-triazol-4-yl,

R represents straight-chain or branched alkyl with 1 to 8 carbon atoms, straight-chain or branched alkenyl or alkynyl with in either case 2 to 4 carbon atoms, halogenoalkyl with 1 or 2 carbon atoms and 1 to 5 halogen atoms, alkoxy with 1 to 4 carbon atoms, alkoxyalkyl with 1 to 4 carbon atoms in each alkyl part, cycloalkyl with 5 to 7 carbon atoms, optionally substituted phenyl or phenylalkyl or phenoxyalkyl, either of which is optionally substituted in the phenyl part and has up to 2 carbon atoms in the alkyl part, the substituents on the phenyl part in the last three cases being selected from halogen, cyano, nitro and alkyl or alkoxy with in either case 1 to 2 carbon atoms, or R represents alkylamino with 1 to 12 carbon atoms, dialkylamino with 1 to 4 carbon atoms in each alkyl part, halogenoalkylamino with up to 4 carbon atoms and up to 5 identical or different halogen atoms, or alkoxycarbonylamino with 1 to 4 carbon atoms in the alkyl part, alkoxyalkylamino with 1 to 4 carbon atoms in each alkyl part or optionally monosubstituted or polysubstituted phenylamino, the substituents being selected from halogen, nitro, cyano, straight-chain or branched alkyl with 1 to 4 carbon atoms, alkoxy and alkylthio with in either case 1 or 2 carbon atoms, halogenoalkyl with up to 2 carbon atoms and up to 5 identical or different halogen atoms and alkoxycarbonylalkenyl with 1 to 4 carbon atoms in the alkyl part and 2 to 4 carbon atoms in the alkenyl part, X represents hydrogen or fluorine, Z represents halogen, and n represents 1 or 2, or a physiologically acceptable acid addition salt thereof with a hydrogen halide acid, phosphoric acid, nitric acid, sulphuric acid, a sulphonic acid or an optionally hydroxy-substituted mono- or dicarboxylic acid, or a complex thereof with a metal salt, the metal of which is copper, zinc, manganese, magnesium, tin, iron or nickel and the anion of which is halide, nitrate, sulphate or phosphate.

2. A compound according to claim 1, wherein such compound is 2-acetoxy-3,3-bisfluoromethyl-1-(4-chlorophenoxy)-1-(1,2,4-triazol-1-yl)-butane of the formula

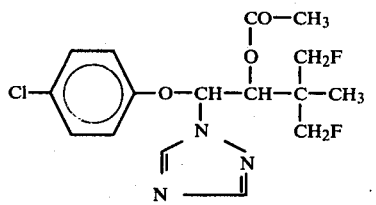

or a salt or complex thereof.

3. A compound according to claim 1, wherein such compound is 2-acetoxy-3-fluoromethyl-3-methyl-1-(4-chlorophenoxy)-1-(1,2,4-triazol-1-yl)-butane of the formula

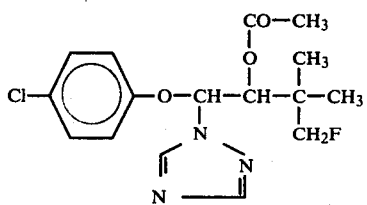

or a salt or complex thereof.

4. A compound according to claim 1, wherein such compound is 2-chloroacetoxy-3,3-bisfluoromethyl-1-(4-chlorophenoxy)-1-(1,2,4-triazol-1-yl)-butane of the formula

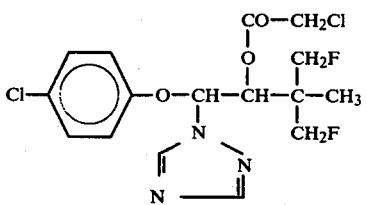

or a salt or complex thereof.

5. A compound according to claim 1, wherein such compound is 2-acetoxy-3,3-bisfluoromethyl-1-(4-fluorophenoxy)-1-(1,2,4-triazol-1-yl)-butane of the formula

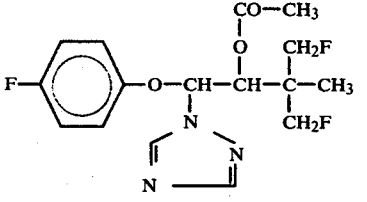

or a salt or complex thereof.

6. A compound according to claim 1, wherein such compound is 2-dichloroacetoxy-3,3-bisfluoromethyl-1-(4-chlorophenoxy)-1-(1,2,4-triazol-1-yl)-butane of the formula

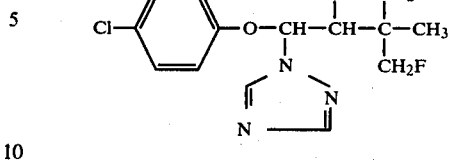

or a salt or complex thereof.

7. A compound according to claim 1, wherein such compound is 2-acetoxy-3,3-bisfluoromethyl-1-(2,4-dichlorophenoxy)-1-(1,2,4-triazol-1-yl)-butane of the formula

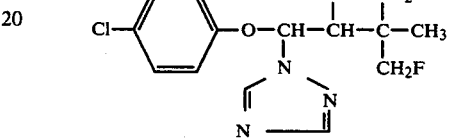

or a salt or complex thereof.

8. A compound according to claim 1, wherein such compound is 2-dichloroacetoxy-3,3-bisfluoromethyl-1-(4-fluorophenoxy)-1-(1,2,4-triazol-1-yl)-butane of the formula

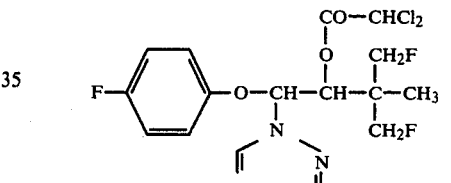

or a salt or complex thereof.

9. A fungicidal composition comprising as active ingredient a fungicidally effective amount of a compound, salt or complex according to claim 1 in admixture with a diluent.

10. A method of combating fungi comprising a fungicidally effective amount of a compound, salt or complex according to claim 1.

11. The method according to claim 10, wherein the compound is 2-acetoxy-3,3-bisfluoromethyl-1-(4-chlorophenoxy)-1-(1,2,4-triazol-1-yl)-butane, 2-acetoxy-3-fluoromethyl-1-(4-chlorophenoxy)-1-(1,2,4-triazol-1-yl)-butane, 2-chloroacetoxy-3,3-bisfluoromethyl-1-(4-chlorophenoxy)-1-(1,2,4-triazol-1-yl)-butane, 2-acetoxy-3,3-bisfluoromethyl-1-(4-fluorophenoxy)-1-(1,2,4-triazol-1-yl)-butane, 2-dichloroacetoxy-3,3-bisfluoromethyl-1-(4-chlorophenoxy)-1-(1,2,4-triazol-1-yl)-butane, 2-acetoxy-3,3-bisfluoromethyl-1-(2,4-dichlorophenoxy)-1-(1,2,4-triazol-1-yl)-butane or 2-dichloroacetoxy-3,3-bisfluoromethyl-1-(4-fluorophenoxy)-1-(1,2,4-triazol-1-yl)-butane, or a salt or complex thereof.

* * * * *